United States Patent
Nicholson

(10) Patent No.: US 11,612,185 B2
(45) Date of Patent: Mar. 28, 2023

(54) ARTICLE FOR USE WITH APPARATUS FOR HEATING SMOKABLE MATERIAL

(71) Applicant: BRITISH AMERICAN TOBACCO (INVESTMENTS) LIMITED, London (GB)

(72) Inventor: Gary Nicholson, London (GB)

(73) Assignee: Nicoventures Trading Limited, London (GB)

( * ) Notice: Subject to any disclaimer, the term of this patent is extended or adjusted under 35 U.S.C. 154(b) by 519 days.

(21) Appl. No.: 16/311,409

(22) PCT Filed: Jun. 27, 2017

(86) PCT No.: PCT/EP2017/065907
§ 371 (c)(1),
(2) Date: Dec. 19, 2018

(87) PCT Pub. No.: WO2018/002084
PCT Pub. Date: Jan. 4, 2018

(65) Prior Publication Data
US 2019/0239555 A1   Aug. 8, 2019

Related U.S. Application Data

(60) Provisional application No. 62/356,339, filed on Jun. 29, 2016.

(51) Int. Cl.
A24F 40/465   (2020.01)
A61M 15/06   (2006.01)
(Continued)

(52) U.S. Cl.
CPC .......... *A24F 40/465* (2020.01); *A24B 15/167* (2016.11); *A24D 1/20* (2020.01);
(Continued)

(58) Field of Classification Search
CPC ..................................................... A24F 40/465
See application file for complete search history.

(56) References Cited

U.S. PATENT DOCUMENTS 4,510,950 A   4/1985 Keritsis
5,369,723 A   11/1994 Counts
(Continued)

FOREIGN PATENT DOCUMENTS

CN   103689812 A   4/2014
EP   0244272   11/1987
(Continued)

OTHER PUBLICATIONS

International Search Report and Written Opinion, Application No. PCT/EP2017/065907, dated Dec. 5, 2017, 24 pages.
(Continued)

*Primary Examiner* — Cynthia Szewczyk
(74) *Attorney, Agent, or Firm* — Patterson Thuente P.A.

(57) ABSTRACT

Disclosed is an article for use with apparatus for heating smokable material to volatilize at least one component of the smokable material. The article includes a foam. The foam includes smokable material, such as tobacco. Also disclosed is a system, comprising an article and apparatus. The article includes a foam including smokable material. The apparatus is for heating the smokable material to volatilize at least one component of the smokable material. The apparatus includes a heating zone for receiving at least a portion of the article.

17 Claims, 4 Drawing Sheets

(51) Int. Cl.
*A24D 1/20* (2020.01)
*A24B 15/167* (2020.01)
*H05B 6/10* (2006.01)
*A24F 40/20* (2020.01)

(52) U.S. Cl.
CPC ............. *A61M 15/06* (2013.01); *H05B 6/105* (2013.01); *A24F 40/20* (2020.01); *A61M 2205/36* (2013.01)

(56) References Cited

U.S. PATENT DOCUMENTS

| | | | |
|---|---|---|---|
| 5,613,505 A * | 3/1997 | Campbell | ............... A24F 40/53 131/194 |
| 5,692,526 A | 12/1997 | Adams | |
| 2007/0102013 A1 | 5/2007 | Adams | |
| 2008/0092912 A1 | 4/2008 | Robinson | |
| 2014/0190496 A1 * | 7/2014 | Wensley | ............. A24B 15/167 131/273 |
| 2014/0301721 A1 | 10/2014 | Ruscio | |
| 2017/0071253 A1 * | 3/2017 | Revell | ...................... H05B 3/44 |
| 2018/0317554 A1 | 11/2018 | Kaufman | |
| 2018/0317555 A1 | 11/2018 | Blandino | |
| 2019/0082738 A1 | 3/2019 | Blandino | |
| 2019/0191780 A1 | 6/2019 | Wilke | |

FOREIGN PATENT DOCUMENTS

| | | |
|---|---|---|
| EP | 0503767 | 9/1992 |
| JP | H05115272 A | 5/1993 |
| JP | H11507234 A | 6/1999 |
| JP | 2007267749 A | 10/2007 |
| JP | 2010506594 A | 3/2010 |
| RU | 2577500 C2 | 3/2016 |
| SU | 1623555 A3 | 1/1991 |
| WO | WO-2014170679 A1 | 10/2014 |
| WO | WO 2015177294 | 1/2015 |
| WO | WO 2015082649 | 6/2015 |
| WO | WO 2015082651 | 6/2015 |
| WO | WO 2015082652 | 6/2015 |
| WO | WO 2015131058 | 9/2015 |
| WO | WO 2015175568 | 11/2015 |
| WO | WO 2015176898 | 11/2015 |
| WO | WO-2015176898 A1 * | 11/2015 ............... A24C 5/01 |
| WO | WO-2015177045 A1 * | 11/2015 ........... A24B 15/167 |
| WO | WO 2015177247 | 11/2015 |
| WO | WO 2015177252 | 11/2015 |
| WO | WO 2015177253 | 11/2015 |
| WO | WO 2015177263 | 11/2015 |
| WO | WO 2016075436 | 5/2016 |
| WO | WO-2017029268 A1 | 2/2017 |
| WO | WO-2017068096 A1 | 4/2017 |
| WO | WO 2017182485 | 10/2017 |
| WO | WO-2018002083 | 1/2018 |

OTHER PUBLICATIONS

Extended European Search Report for Application No. EP20204765.0, dated Jan. 19, 2021, 23 pages.
International Preliminary Report on Patentability for Application No. PCT/EP2017/065907, dated Jan. 10, 2019, 16 pages.
Office Action for Japanese Application No. 2018-567858, dated Dec. 1, 2020, 8 pages.
Office Action For Korean Application No. 10-2018-7037694, dated Apr. 29, 2021, 10 pages.
Office Action For Russian Application No. 2020135850, dated Apr. 15, 2021, 17 pages.
Office Action dated Mar. 24, 2020 for Japanese Application No. 2018-567858, 6 pages.
Office Action dated Sep. 26, 2019 for Russian Patent Application No. 2018146098, 11 pages.
Russian Office Action for RU Application No. 2018146098 dated Oct. 23, 2019.

* cited by examiner

ARTICLE FOR USE WITH APPARATUS FOR HEATING SMOKABLE MATERIAL

PRIORITY CLAIM

The present application is a National Phase entry of PCT Application No. PCT/EP2017/065907, filed Jun. 27, 2017, which claims priority from Provisional Application No. 62/356,339, filed Jun. 29, 2016, each of which is hereby fully incorporated herein by reference.

TECHNICAL FIELD

The present disclosure relates to articles for use with an apparatus for heating smokable material to volatilize at least one component of the smokable material, and to systems comprising such an apparatus and such articles.

BACKGROUND

Smoking articles such as cigarettes, cigars and the like burn tobacco during use to create tobacco smoke. Attempts have been made to provide alternatives to these articles by creating products that release compounds without combusting. Examples of such products are so-called "heat not burn" products or tobacco heating devices or products, which release compounds by heating, but not burning, material. The material may be, for example, tobacco or other non-tobacco products, which may or may not contain nicotine.

SUMMARY

A first aspect of the present disclosure provides an article for use with an apparatus for heating smokable material to volatilize at least one component of the smokable material, the article including a foam comprising smokable material.

In an exemplary embodiment, the foam comprises gas dispersed in a solid medium.

In an exemplary embodiment, the solid medium comprises the smokable material.

In an exemplary embodiment, the solid medium comprises a carrier.

In an exemplary embodiment, the carrier comprises cellulose or starch, such as starch-lignin.

In an exemplary embodiment, the foam is an open-cell foam.

In an exemplary embodiment, the foam extends from one end of the article to an opposite end of the article.

In an exemplary embodiment, a first portion of the foam has a first density, a second portion of the foam has a second density, and the second density is greater than the first density.

In an exemplary embodiment, the article is elongate, and the first and second portions of the foam are located at different positions along a length of the article.

In an exemplary embodiment, the article further comprises heating material that is heatable by penetration with a varying magnetic field, and the heating material is in thermal contact with the smokable material.

In an exemplary embodiment, the foam is fixed or adhered to the heating material.

In an exemplary embodiment, the heating material is in the form of a body that extends from one end of the article to an opposite end of the article.

In an exemplary embodiment, the heating material comprises one or more materials selected from the group consisting of: an electrically-conductive material, a magnetic material, and a magnetic electrically-conductive material.

In an exemplary embodiment, the heating material comprises a metal or a metal alloy.

In an exemplary embodiment, the heating material comprises one or more materials selected from the group consisting of: aluminum, gold, iron, nickel, cobalt, conductive carbon, graphite, plain-carbon steel, stainless steel, ferritic stainless steel, copper, and bronze.

In an exemplary embodiment, the article comprises elements disbursed through the foam, each of the elements comprises heating material that is heatable by penetration with a varying magnetic field, and the heating material is in thermal contact with the smokable material.

In an exemplary embodiment, the elements are disbursed evenly, or substantially evenly, through the foam.

In an exemplary embodiment, each of the elements comprises a closed circuit of the heating material.

In an exemplary embodiment, the article is free from heating material that is heatable by penetration with a varying magnetic field.

In an exemplary embodiment, the smokable material comprises tobacco and/or one or more humectants.

In an exemplary embodiment, the article comprises a cover around the foam.

In an exemplary embodiment, the cover comprises a wrapper or a sheet of paper.

A second aspect of the present disclosure provides a system, comprising: an article including a foam comprising smokable material; and an apparatus for heating the smokable material to volatilize at least one component of the smokable material, wherein the apparatus comprises a heating zone for receiving at least a portion of the article.

In an exemplary embodiment, the apparatus is for heating the smokable material to volatilize at least one component of the smokable material without combusting the smokable material.

In an exemplary embodiment, the article of the system of the second aspect is the article of the first aspect. The article of the system of the second aspect may have any one or more of the features discussed above as being present in respective exemplary embodiments of the article of the first aspect.

BRIEF DESCRIPTION OF THE DRAWINGS

Embodiments of the disclosure will now be described, by way of example only, with reference to the accompanying drawings, in which.

DETAILED DESCRIPTION

Figure 1:
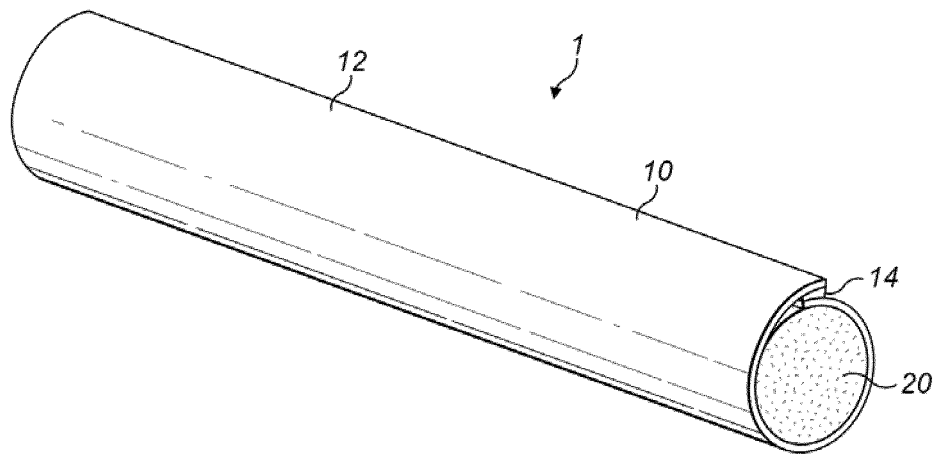
FIG. 1 shows a schematic perspective view of an example of an article for use with an apparatus for heating smokable material to volatilize at least one component of the smokable material.

As used herein, the term "smokable material" includes materials that provide volatilized components upon heating, typically in the form of vapor or an aerosol. "Smokable material" may be a non-tobacco-containing material or a tobacco-containing material. "Smokable material" may, for example, include one or more of tobacco per se, tobacco derivatives, expanded tobacco, reconstituted tobacco, tobacco extract, homogenized tobacco or tobacco substitutes. The smokable material can be in the form of ground tobacco, cut rag tobacco, extruded tobacco, reconstituted tobacco, reconstituted smokable material, liquid, gel, gelled sheet, powder, or agglomerates, or the like. "Smokable material" also may include other, non-tobacco, products, which, depending on the product, may or may not contain nicotine. "Smokable material" may comprise one or more humectants, such as glycerol or propylene glycol.

As used herein, the term "foam" includes substances comprising gas dispersed in a liquid medium or in a solid medium. In some embodiments, the foam comprises a gas dispersed in a solid medium, and the solid medium comprises the smokable material. In some embodiments, the solid medium consists of, or consists substantially entirely of, the smokable material. The foam may be an open-cell foam, a closed-cell foam, or a foam comprising both open and closed cells. In some embodiments, an open-cell foam may allow fluid flow through the foam to pick up volatilized components of the smokable material in use. In some embodiments, a closed-cell foam may be porous to allow fluid flow through the foam to pick up volatilized components of the smokable material in use. In some embodiments, the foam may be a closed-cell foam that becomes an open-cell foam upon heating.

In some embodiments, the solid medium comprises a carrier, which may for example be cellulose or starch, such as starch-lignin. The smokable material may be mixed with the carrier. In some embodiments, the solid material may be thermally conductive to promote heat transfer. In some embodiments, as discussed below, the solid material may comprise heating material that is heatable by penetration with a varying magnetic field.

As used herein, the term "heating material" or "heater material" refers to material that is heatable by penetration with a varying magnetic field.

Induction heating is a process in which an electrically-conductive object is heated by penetrating the object with a varying magnetic field. The process is described by Faraday's law of induction and Ohm's law. An induction heater may comprise an electromagnet and a device for passing a varying electrical current, such as an alternating current, through the electromagnet. When the electromagnet and the object to be heated are suitably relatively positioned so that the resultant varying magnetic field produced by the electromagnet penetrates the object, one or more eddy currents are generated inside the object. The object has a resistance to the flow of electrical currents. Therefore, when such eddy currents are generated in the object, their flow against the electrical resistance of the object causes the object to be heated. This process is called Joule, ohmic, or resistive heating. An object that is capable of being inductively heated is known as a susceptor.

It has been found that, when the susceptor is in the form of a closed circuit, magnetic coupling between the susceptor and the electromagnet in use is enhanced, which results in greater or improved Joule heating.

Magnetic hysteresis heating is a process in which an object made of a magnetic material is heated by penetrating the object with a varying magnetic field. A magnetic material can be considered to comprise many atomic-scale magnets, or magnetic dipoles. When a magnetic field penetrates such material, the magnetic dipoles align with the magnetic field. Therefore, when a varying magnetic field, such as an alternating magnetic field, for example as produced by an electromagnet, penetrates the magnetic material, the orientation of the magnetic dipoles changes with the varying applied magnetic field. Such magnetic dipole reorientation causes heat to be generated in the magnetic material.

When an object is both electrically-conductive and magnetic, penetrating the object with a varying magnetic field can cause both Joule heating and magnetic hysteresis heating in the object. Moreover, the use of magnetic material can strengthen the magnetic field, which can intensify the Joule heating.

In each of the above processes, as heat is generated inside the object itself, rather than by an external heat source by heat conduction, a rapid temperature rise in the object and more uniform heat distribution can be achieved, particularly through selection of suitable object material and geometry, and suitable varying magnetic field magnitude and orientation relative to the object. Moreover, as induction heating and magnetic hysteresis heating do not require a physical connection to be provided between the source of the varying magnetic field and the object, design freedom and control over the heating profile may be greater, and cost may be lower.

Referring to FIG. 1 there is shown a schematic perspective view of an example of an article according to an embodiment of the disclosure. The article 1 comprises a foam 20 that comprises smokable material. The article 1 is for use with an apparatus for heating the smokable material to volatilize at least one component of the smokable material without burning the smokable material, such as the apparatus 100 shown in FIG. 9 and described below.

In this embodiment, the foam 20 is in the form of a cylindrical rod. The rod has a substantially circular cross-section. The foam extends from one end of the article 1 to an opposite end of the article. Thus, in use, air may be drawn into the foam 20 at one end of the article 1, the air may pass through the foam 20 and pick up volatilized components released from the smokable material, and then the volatilized components, typically in the form of vapor or an aerosol, may be drawn out of the foam 20 at the opposite end of the article 1. In this embodiment in which the article 1 is elongate, these ends of the article 1 between which the foam 20 extends are opposite longitudinal ends of the article 1. However, in other embodiments, the ends may be any two ends or sides of the article, such as any two opposite ends or sides of the article.

In this embodiment, the foam 20 comprises gas dispersed in a solid medium. That is, walls of cells of the foam 20 are made of a solid as opposed to, say, a liquid. The solid medium comprises a carrier and the smokable material. The carrier comprises cellulose or starch, but in other embodiments other materials may be used. In this embodiment, the gas is air, but in other embodiments one or more other gases could be used, such as oxygen.

In the article 1 of this embodiment, the foam 20 is an open-cell foam. The use of an open-cell foam facilitates the flow of air drawn into the foam 20 and through the foam 20 by a user. Moreover, when the smokable material is heated in use, the open-cell nature of the foam 20 facilitates the flow of volatilized components released from the smokable material, typically in the form of vapor or an aerosol, through and out of the foam 20 as drawn by a user.

In this embodiment, the foam 20 has a density of about 300 Kg/m$^3$, although in other embodiments the density may be a density less than 500 Kg/m$^3$, such as a density of between 200 Kg/m$^3$ and 400 Kg/m$^3$. The density of the foam 20 may be chosen to help deliver desired levels of thermal conductivity of the foam 20, and/or water retention of the foam 20, and/or ease of fluid flow through the foam 20 in use.

The article 1 of this embodiment has a cover 10 around the foam 20. The cover 10 helps to protect the foam 20 from damage during transport and use of the article 1. During use, the cover 10 may also help to direct the flow of air into and through the foam 20, and help to direct the flow of vapor or aerosol through and out of the foam 20.

In this embodiment, the cover 10 comprises a wrapper 12 that is wrapped around the foam 20 so that free ends of the wrapper 12 overlap each other. The wrapper 12 thus forms all of, or a majority of, a circumferential outer surface of the article 1. The wrapper 12 may be formed from paper, reconstituted smokable material, such as reconstituted tobacco, or the like. The cover 10 of this embodiment also comprises an adhesive 14 that adheres the overlapped free ends of the wrapper 12 to each other. The adhesive may comprise one or more of, for example, gum Arabic, natural or synthetic resins, starches, and varnish. The adhesive 14 helps prevent the overlapped free ends of the wrapper 12 from separating. It is to be noted that the size of the adhesive 14 relative to the wrapper 12 is accentuated in FIG. 1 for clarity.

The cover 10 defines an outer surface of the article 1 and may contact the apparatus in use. In this embodiment, the article 1 is elongate and cylindrical with a substantially circular cross-section. However, in other embodiments, the article may have a cross-section other than circular and/or not be elongate and/or not be cylindrical. In this embodiment, the article 1 has proportions approximating those of a cigarette. The cover 10 may be made of a thermally-conductive material, for transferring heat energy from the apparatus to the foam 20 in use.

Figure 2:
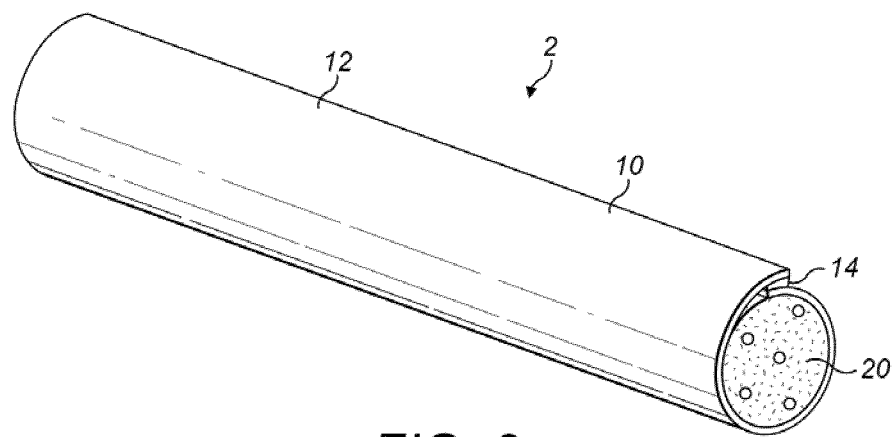
FIG. 2 shows a schematic perspective view of an example of another article for use with an apparatus for heating smokable material to volatilize at least one component of the smokable material.
Figure 3:
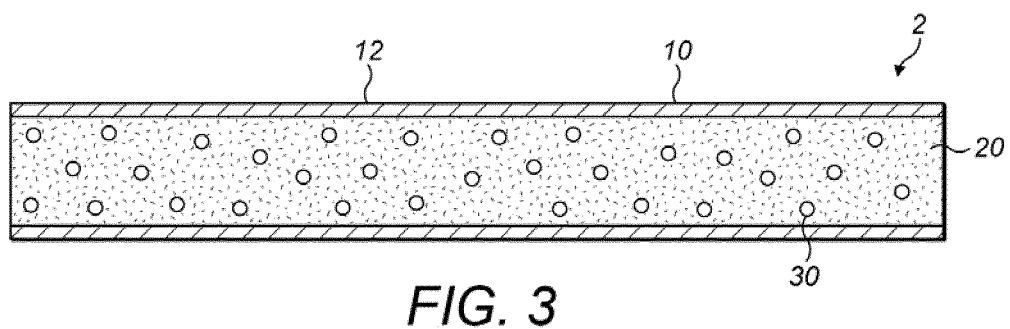
FIG. 3 shows a schematic cross-sectional view of the article of FIG. 2.

Referring to FIGS. 2 and 3 there are shown a schematic perspective view and a schematic cross-sectional view of an example of another article according to an embodiment of the disclosure. The article 1 of FIG. 1 is free from heating material that is heatable by penetration with a varying magnetic field. The article 2 of FIGS. 2 and 3 is identical to the article 1 of FIG. 1, except that the article 2 of FIGS. 2 and 3 comprises such heating material. Therefore, in the interests of conciseness features common to the two embodiments will not be described again in detail. The article 2 is for use with an apparatus for heating the smokable material to volatilize at least one component of the smokable material without burning the smokable material, such as the apparatus 100 shown in FIG. 9 and described below. Any of the herein-described possible variations to the article 1 of FIG. 1 may be made to the article 2 of FIGS. 2 and 3 to form separate respective embodiments.

In this embodiment, in addition to the cover 10 and the foam 20, the article 2 comprises heating material that is heatable by penetration with a varying magnetic field. The heating material is in thermal contact with the smokable material. Therefore, the heating material is heatable in use to heat the smokable material. More specifically, the article 2 comprises elements 30 disbursed through the foam 20, and each of the elements 30 comprises the heating material. The elements 30 are disbursed evenly, or substantially evenly, through the foam 20. This substantially even distribution helps to provide substantially even heating of the smokable material in use. In other embodiments, the elements 30 may instead be disbursed through the foam 20 unevenly so that a first region of the article has a greater density or proportion of heating material than a second region. Such uneven distribution of the elements 30 could help provide progressive heating of the smokable material in use, as the smokable material in the first region may be heated more quickly than the second region, so that the first region releases volatilized components before the second region. The first region may also reach a higher maximum temperature than the second region in use.

In this embodiment, each of the elements 30 comprises a closed circuit of the heating material. More specifically, each of the elements 30 is loop-shaped. Yet more specifically, in this embodiment, each of the elements 30 is ring-shaped. A loop-shaped element may be of any shape that defines a path that starts and ends at the same point so as to create a closed circuit, whereas a ring-shaped element necessarily is circular or substantially circular. A ring shaped element has a relatively a large surface area to weight ratio, which can help to avoid the elements 30 tending to cluster by settling due to gravity. A ring shaped element can have a small cross-sectional area to diameter ratio. Therefore, the circulating current in the ring when subjected to a varying magnetic field may penetrate most or all of the ring, rather than be confined to just a "skin" thereof, as can be the case when a susceptor has too great a thickness. Thus, a more efficient use of material is achieved and, in turn, costs are reduced. In this embodiment, each of the elements 30 consists entirely, or substantially entirely, of the heating material. However, in other embodiments, one or more of the elements 30 may comprise a loop- or ring-shaped body that is free from heating material and that carries the closed circuit of heating material. For example, one or more of the elements may comprise a ring-shaped body free from heating material with a closed-circuit of the heating material coated thereon.

In variations to this embodiment, some or each of the elements 30 may be irregularly-shaped, spherical, a particle, or a discrete strand. When discrete strands of the heating material are provided, the strands may overlap and/or contact one another to define one or more closed circuits of the heating material. The strands may all be made of the same heating material. The strands may be linear or curved, for example, such as helical. In some embodiments, as mentioned above, each of the elements 30 may comprise a body that is free from heating material and that carries heating material. The heating material carried by the body may be in the form of a closed circuit.

In variations to the illustrated embodiment, the heating material may not form closed circuits. That is, the elements 30 may be free from closed circuits of heating material.

In some embodiments, the elements 30 may comprise elements of a first material and elements of a second material that is different from the first material. The first and second materials may be heatable by a given varying magnetic field at different rates.

Figure 4:
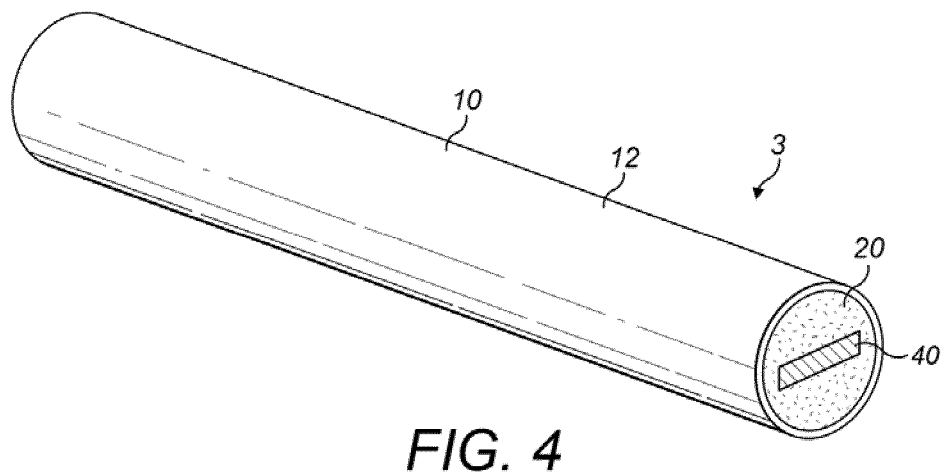
FIG. 4 shows a schematic perspective view of an example of another article for use with an apparatus for heating smokable material to volatilize at least one component of the smokable material.
Figure 5:
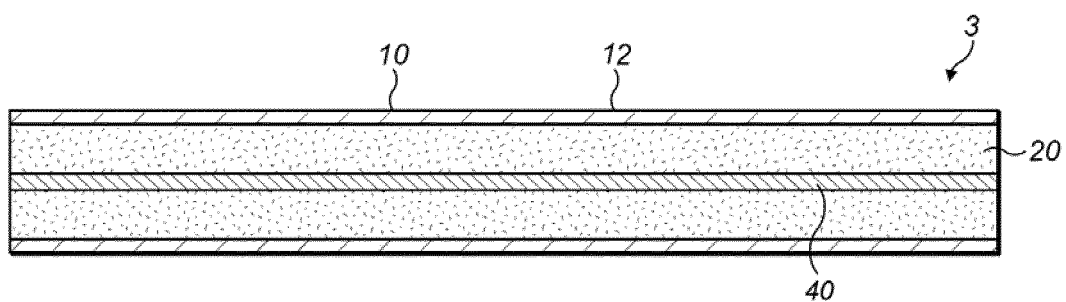
FIG. 5 shows a schematic cross-sectional view of the article of FIG. 4.

Referring to FIGS. 4 and 5 there are shown a schematic perspective view and a schematic cross-sectional view of an example of another article according to an embodiment of the disclosure. The article 3 of FIGS. 4 and 5 is identical to the article 1 described above with reference to FIG. 1, except that the article 3 comprises heating material that is heatable by penetration with a varying magnetic field. Therefore, in the interests of conciseness features common to the two embodiments will not be described again in detail. The article 3 is for use with an apparatus for heating the smokable material to volatilize at least one component of the smokable material without burning the smokable material, such as the apparatus 100 shown in FIG. 9 and described below. Any of the herein-described possible variations to the article 1 of FIG. 1 may be made to the article 3 of FIGS. 4 and 5 to form separate respective embodiments.

In this embodiment, in addition to the cover 10 and the foam 20, the article 3 comprises heating material that is heatable by penetration with a varying magnetic field. More specifically, the article 2 comprises a body of the heating material 40 within the foam 20. The heating material is in thermal contact with the smokable material. Therefore, the heating material is heatable in use to heat the smokable material. In this embodiment, the foam 20 is fixed to the heating material of the body 40. This is achieved by adhering the foam 20 to the body 40. However, in other embodiments, the fixing may be by other than adhesion. In some embodiments the foam 20 may not be fixed to the heating material as such.

In this embodiment, the body of heating material 40 is elongate and extends from one end of the foam 20 to an opposite end of the foam 20. This can help to provide more uniform heating of the smokable material of the foam 20 in use. However, in other embodiments, the body of heating material 40 may not extend to either of the opposite ends of the foam 20, or may extend to only one of the ends of the foam 20 and be spaced from the other of the ends of the foam 20.

In this embodiment, the body of heating material 40 extends from one end of the article 3 to an opposite end of the article 3. This can aid manufacturing of the article 3. However, in other embodiments, the body of heating material 40 may not extend to either of the opposite ends of the article 3, or may extend to only one of the ends of the article 3 and be spaced from the other of the ends of the article 3.

In this embodiment, the body of heating material 40 extends along a longitudinal axis that is substantially aligned with a longitudinal axis of the article 3. This can aid manufacturing of the article 3. In this embodiment, the aligned axes are coincident. In a variation to this embodiment, the aligned axes may be parallel to each other. However, in other embodiments, the axes may be oblique to each other.

In this embodiment, the body of heating material 40 is encircled by the foam 20. That is, the foam 20 extends around the body of heating material 40. In embodiments in which the body of heating material 40 does not extend to either of the opposite ends of the foam 20, the foam 20 may extend around the body of heating material 40 and also cover the ends of the body of heating material 40, so that the body of heating material 40 is surrounded by the foam 20.

In this embodiment, the body 40 is impermeable to air or volatilized material, and is substantially free from discontinuities. The body 40 may thus be relatively easy to manufacture. However, in variations to this embodiment, the body 40 may be permeable to air and/or permeable to volatilized material created when the smokable material is heated. Such a permeable nature of the body 40 may help air passing through the article 3 to pick up the volatilized material created when the smokable material is heated.

In this embodiment, the body of heating material 40 has a rectangular, or substantially rectangular, cross-section perpendicular to its length. The body of heating material 40 has two opposing major surfaces joined by two minor surfaces. Therefore, the depth or thickness of the body 40 is relatively small as compared to the other dimensions of the body 40. However, in other embodiments, the body 40 may have a cross-section that is a shape other than rectangular, such as circular, elliptical, annular, polygonal, square, triangular, X-shaped, T-shaped, star-shaped, or radially-finned.

In this embodiment, the cross-section of the body of heating material 40 is constant along the length of the body 40. Moreover, in this embodiment, the body of heating material 40 is planar, or substantially planar. The body of heating material 40 of this embodiment can be considered a flat strip or ribbon. However, in other embodiments, this may not be the case.

In some embodiments, the body of heating material 40 may be non-planar. For example, the body 40 may follow a wavelike or wavy path, be twisted, be corrugated, be helical, have a spiral shape, comprise a plate or strip or ribbon having protrusions thereon and/or indentations therein, comprise a mesh, comprise expanded metal, or have a non-uniform non-planar shape. Such non-planar shapes may help air passing through the article to pick up the volatilized material created when the smokable material is heated. Non-planar shapes can provide a tortuous path for air to follow, creating turbulence in the air and causing better heat transfer from the heating material to the smokable material. The non-planar shapes can also increase the surface area of the body of heating material 40 per unit length of the body 40. This can result in greater or improved Joule heating of the body 40, and thus greater or improved heating of the smokable material. In some embodiments, the body of heating material 40 may be hollow or perforated.

Figure 6:
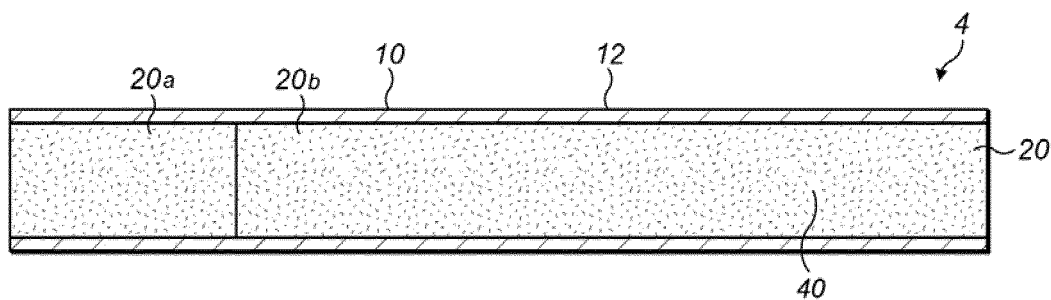
FIG. 6 shows a schematic cross-sectional view of an example of another article for use with an apparatus for heating smokable material to volatilize at least one component of the smokable material.
Figure 7:
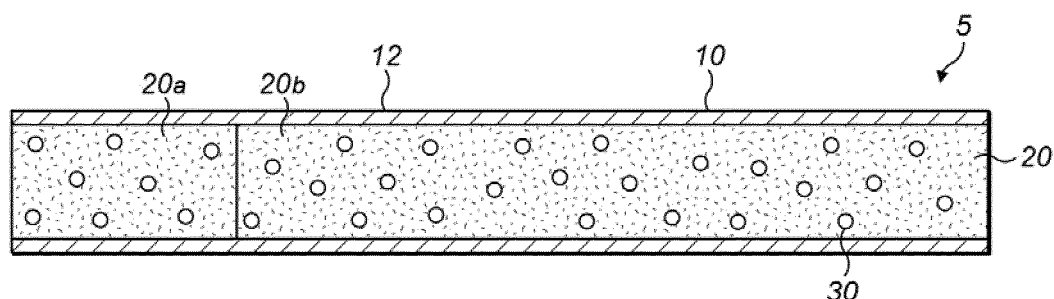
FIG. 7 shows a schematic cross-sectional view of an example of another article for use with an apparatus for heating smokable material to volatilize at least one component of the smokable material.
Figure 8:
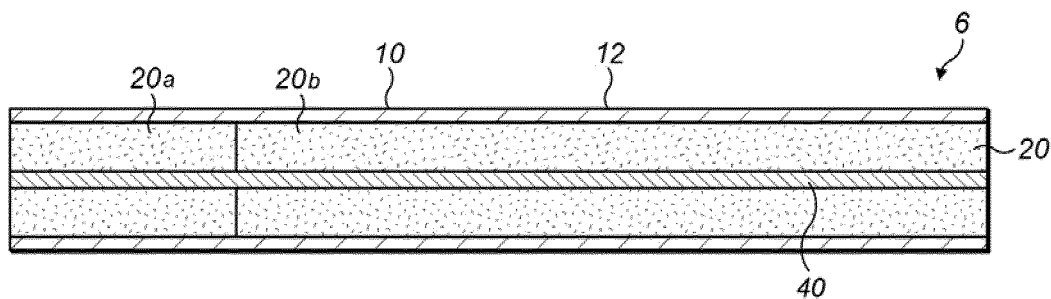
FIG. 8 shows a schematic cross-sectional view of an example of another article for use with an apparatus for heating smokable material to volatilize at least one component of the smokable material.

Referring to FIGS. 6, 7 and 8 there are shown schematic cross-sectional views of examples of other articles according to respective embodiments of the disclosure. The article 4 of FIG. 6 is identical to the article 1 described above with reference to FIG. 1, except for the form of the foam 20 of the article 1. The article 5 of FIG. 7 is identical to the article 2 described above with reference to FIGS. 2 and 3, except for the form of the foam 20 of the article 5. The article 6 of FIG. 8 is identical to the article 3 described above with reference to FIGS. 4 and 5, except for the form of the foam 20 of the article 6. In the interests of conciseness, features common to two embodiments will not be described again in detail. Each of the articles 4, 5, 6 is for use with an apparatus for heating the smokable material to volatilize at least one component of the smokable material without burning the smokable material, such as the apparatus 100 shown in FIG. 9 and described below.

Any of the herein-described possible variations to the article 1 of FIG. 1 may be made to the article 4 of FIG. 6 to form separate respective embodiments. Similarly, any of the herein-described possible variations to the article 2 of FIGS. 2 and 3 may be made to the article 5 of FIG. 7 to form separate respective embodiments, and any of the herein-described possible variations to the article 3 of FIGS. 4 and 5 may be made to the article 6 of FIG. 8 to form separate respective embodiments.

In each of the articles 4, 5, 6 of FIGS. 6, 7 and 8, a first portion 20a of the foam 20 has a first density and a second portion 20b of the foam 20 has a second density. In these embodiments the second density is greater than the first density, but in respective variations to these embodiments the first density may be greater than the second density. As will be appreciated from consideration of the Figures, the first and second portions 20a, 20b of the foam 20 are located at different positions along the length of the elongate articles 4, 5, 6. Therefore, in use, vapor or aerosol flows from one of the first and second portion 20a, 20b of the foam 20 to and through the other of the first and second portions 20a, 20b of the foam 20. The first and second portions 20a, 20b of the foam 20 may be held together by the cover 10.

Providing the first and second portions 20a, 20b of the foam 20 with different respective densities may help to determine or affect different relative characteristics of the first and second portions 20a, 20b of the foam 20, such as their relative strengths, their relative masses, their relative thermal conductivities, their relative resistances to airflow, the relative amounts of smokable material they contain, and their relative rates of releasing volatilized components of the smokable material in use. The densities may also help determine or affect the centre of mass of the article.

Foams that have different densities but are otherwise identical may heat at different rates in use. Therefore, by providing the first and second portions 20a, 20b of foam 20 with different densities, progressive heating of the article 4 by heating of the heating material may be provided.

In the embodiment of FIG. 7, the elements 30 comprising heatable material are disbursed evenly, or substantially evenly, through all the foam 20. Alternatively, in other embodiments, the density of distribution of the elements 30 in the first portion 20a of the foam 20 may differ to that in the second portion 20b of the foam 20. For example, there may be less dense distribution of the elements 30 in the first portion 20a of the foam 20 than in the second portion 20b of the foam 20, or there may be less dense distribution of the elements 30 in the second portion 20b of the foam 20 than in the first portion 20a of the foam 20.

In variations to the embodiment of FIG. 8, the density of the foam 20 could instead vary with distance from the body of heating material 40, or could vary with both distance from and distance along the body of heating material 40. This may help to tailor the release of aerosol as the article is heated in use. For example, the first and second portions of the foam 20 may be arranged with the relatively denser portion of foam closer to the body of heating material 40 than the less dense portion of foam. Alternatively, the less dense portion of foam may be closer to the body of heating material 40 than the relatively denser portion of the foam. For example, in some embodiments, one of the first and second portions of foam may be tubular and encircling the body of heating material 40, and the other of the first and second portions of foam may be tubular and encircling the other of the first and second portions of foam.

In each of the embodiments discussed above that comprises heating material, the heating material is steel. However, in other embodiments, the heating material may comprise one or more materials selected from the group consisting of: an electrically-conductive material, a magnetic material, and a magnetic electrically-conductive material. In some embodiments, the heating material may comprise a metal or a metal alloy. In some embodiments, the heating material may comprise one or more materials selected from the group consisting of: aluminum, gold, iron, nickel, cobalt, conductive carbon, graphite, plain-carbon steel, stainless steel, ferritic stainless steel, copper, and bronze. Other heating material(s) may be used in other embodiments. It has been found that, when magnetic electrically-conductive material is used as the heating material, magnetic coupling between the magnetic electrically-conductive material and an electromagnet of the apparatus in use may be enhanced. In addition to potentially enabling magnetic hysteresis heating, this can result in greater or improved Joule heating of the heating material, and thus greater or improved heating of the smokable material.

In each of the articles 2, 3, 5, 6 shown in FIGS. 2 to 8, the heating material is in surface contact with the smokable material. Thus, when the heating material is heated by penetration with a varying magnetic field, heat may be transferred directly from the heating material to the smokable material. In other embodiments, the heating material may be kept out of surface contact with the smokable material. For example, in some embodiments, the article 2, 3, 5, 6 may comprise a thermally-conductive barrier that is free from heating material and that spaces the heating material from the smokable material. In some embodiments, the thermally-conductive barrier may be a coating on the heating material. The provision of such a barrier may be advantageous to help to dissipate heat to alleviate hot spots in the heating material.

The heating material may have a skin depth, which is an exterior zone within which most of an induced electrical current and/or induced reorientation of magnetic dipoles occurs. By providing that the heating material has a relatively small thickness, a greater proportion of the heating material may be heatable by a given varying magnetic field, as compared to heating material having a depth or thickness that is relatively large as compared to the other dimensions of the heating material. Thus, a more efficient use of material is achieved and, in turn, costs are reduced.

The use of a foam may help to provide a large surface area from which volatilized components of the smokable material may be picked up by fluid flow through the foam in use. The use of a foam may, for example, enhance thermal conductivity in the article as compared, say, to a cut-rag smokable material rod. In turn, this may help provide faster and/or more even heating of the smokable material, or the article as a whole. The use of a foam and the characteristics of the foam may also help to determine the strength of the article, the thermal conductivity of the article, and the resistance to airflow through the article.

The foam may comprise smokable material, a binder (such as sodium alginate), a foam enhancer (such as hydroxypropyl cellulose (HPC)), and an aerosol forming agent (such as glycerol, propylene glycol, triacetin, or diethylene glycol).

In some embodiments, the foam may be manufactured by hydrating a material (such as an alginate, e.g. sodium alginate) to form a paste. An aerosol forming agent and smokable material (such as in the form of ground smokable material) may be added to the paste. A foam enhancer (such as hydroxypropyl cellulose (HPC)) may be added, which may help to trap a gas (such as air) to form a foam. A citrate (such as sodium citrate or calcium citrate) may be added to help retain the structure of the foam.

In some embodiments, the foam may be made as a sheet, and then rolled or coiled for use in an article embodying the disclosure. Alternatively, the foam may be made as a sheet, and then a portion of the foam for use in an article embodying the disclosure may be punched or cut from the sheet. Alternatively, the foam may be made as a sheet, and then shredded for use in an article embodying the disclosure. The formed shreds of foam may be combined to form a rod.

In some embodiments, the foam may be made from a sheet material (comprising smokable material) that is manufactured using a bandcast process. This process itself gives the sheet material some porosity. In order to increase the fill value of the sheet material, foaming may be introduced to increase structural voids at a reduced density. It is possible to tailor the porosity, density, and pore size of the sheet material accordingly. Activated carbon may be incorporated into the sheet material, for example in an amount of 4 to 7.5% (such as wt %). It has been found that a significant portion of the carbon's microstructure may be maintained and not covered by the sheet making process.

In some embodiments, the foam may comprise reconstituted smokable material, such as reconstituted tobacco. During manufacture of reconstituted smokable material, there is flexibility to introduce ingredient(s) that could enhance foaming, such as during separate processing of a base web/fiber and a liquid extract.

The above two processes may be usable to form sheet material that is pliable, yet has sufficiently low density and high firmness to allow good pressure drop, and thus good aerosol flow through the material in use.

In some embodiments, the smokable material may be applied as an extract to a foam substrate. The foam substrate may be foamed reconstituted smokable material or foamed inert material. The inert material may be free from smokable material.

Each of the above-described articles 1, 2, 3, 4, 5, 6 and described variants thereof may be used with an apparatus for heating the smokable material to volatilize at least one component of the smokable material. The apparatus may be to heat the smokable material to volatilize the at least one component of the smokable material without burning the smokable material. Any one of the article(s) 1, 2, 3, 4, 5, 6 and such apparatus may be provided together as a system. The system may take the form of a kit, in which the article 1, 2, 3, 4, 5, 6 is separate from the apparatus. Alternatively, the system may take the form of an assembly, in which the article 1, 2, 3, 4, 5, 6 is combined with the apparatus. An example system will now be described with reference to FIG. 9.

Figure 9:
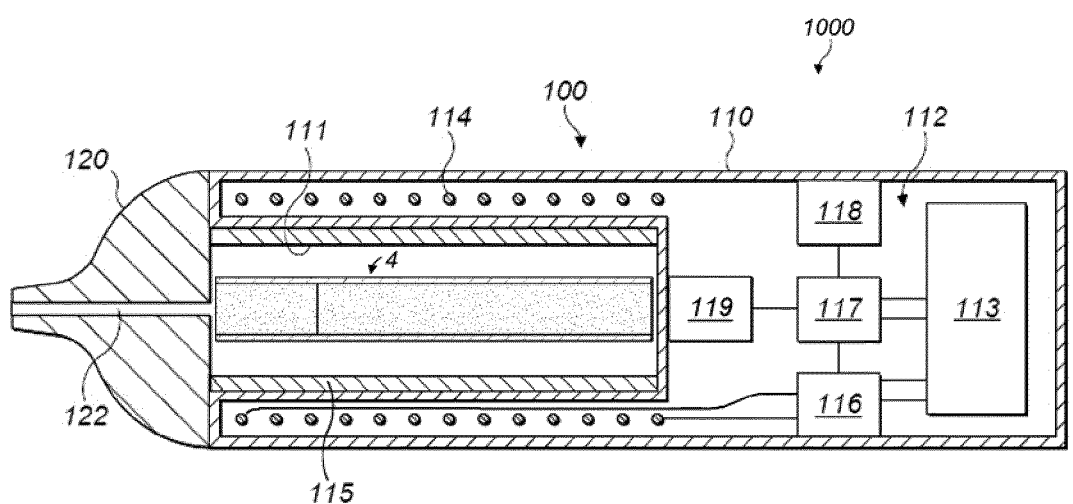
FIG. 9 shows a schematic cross-sectional view of an example of an apparatus for heating smokable material to volatilize at least one component of the smokable material.

Referring to FIG. 9 there is shown a schematic cross-sectional view of an example of a system according to an embodiment of the disclosure. The system 1000 of this embodiment comprises an article 4 comprising a foam comprising smokable material, and apparatus 100 for heating the smokable material of the article 4 to volatilize at least one component of the smokable material. In this embodiment, the article 4 of the system 1000 is the article 4 of FIG. 6. However, in other embodiments, the article of the system 1000 may be an article other than the article 4 of FIG. 6, such as one of the articles 1, 2, 3, 5, 6 of FIGS. 1 to 5, 7 and 8. Broadly speaking, the apparatus 100 comprises a heating zone 111 for receiving at least a portion of the article 4. In this embodiment, the apparatus 100 comprises a heater 115 for heating the heating zone 111, wherein the heater 115 comprises heating material that is heatable by penetration with a varying magnetic field; and a magnetic field generator 112 for generating a varying magnetic field that penetrates the heating material of the heater 115.

The apparatus 100 of this embodiment comprises a body 110 and a mouthpiece 120. The mouthpiece 120 may be made of any suitable material, such as a plastics material, cardboard, cellulose acetate, paper, metal, glass, ceramic, or rubber. The mouthpiece 120 defines a channel 122 therethrough. The mouthpiece 120 is locatable relative to the body 110 so as to cover an opening into the heating zone 111. When the mouthpiece 120 is so located relative to the body 110, the channel 122 of the mouthpiece 120 is in fluid communication with the heating zone 111. In use, the channel 122 acts as a passageway for permitting volatilized material to pass from an article inserted in the heating zone 111 to an exterior of the apparatus 100. In this embodiment, the mouthpiece 120 of the apparatus 100 is releasably engageable with the body 110 so as to connect the mouthpiece 120 to the body 110. In other embodiments, the mouthpiece 120 and the body 110 may be permanently connected, such as through a hinge or flexible member. In some embodiments, such as embodiments in which the article itself comprises a mouthpiece, the mouthpiece 120 of the apparatus 100 may be omitted.

The apparatus 100 may define an air inlet that fluidly connects the heating zone 111 with the exterior of the apparatus 100. Such an air inlet may be defined by the body 110 of the apparatus 100 and/or by the mouthpiece 120 of the apparatus 100. A user may be able to inhale the volatilized component(s) of the smokable material by drawing the volatilized component(s) through the channel 122 of the mouthpiece 120. As the volatilized component(s) are removed from the article, air may be drawn into the heating zone 111 via the air inlet of the apparatus 100.

In this embodiment, the body 110 comprises the heating zone 111. In this embodiment, the heating zone 111 comprises a recess 111 for receiving at least a portion of the article 4. In other embodiments, the heating zone 111 may be other than a recess, such as a shelf, a surface, or a projection, and may require mechanical mating with the article 1, 2, 3, 4, 5, 6 in order to co-operate with, or receive, the article 1, 2, 3, 4, 5, 6. In this embodiment, the heating zone 111 is elongate, and is sized and shaped to receive the article 4. In this embodiment, the heating zone 111 accommodates the whole article 4. In other embodiments, the heating zone 111 may be dimensioned to receive only a portion of the article 1, 2, 3, 4, 5, 6.

In this embodiment, the magnetic field generator 112 comprises an electrical power source 113, a coil 114, a device 116 for passing a varying electrical current, such as an alternating current, through the coil 114, a controller 117, and a user interface 118 for user-operation of the controller 117.

In this embodiment, the electrical power source 113 is a rechargeable battery. In other embodiments, the electrical power source 113 may be other than a rechargeable battery, such as a non-rechargeable battery, a capacitor, a battery-capacitor hybrid, or a connection to a mains electricity supply.

The coil 114 may take any suitable form. In this embodiment, the coil 114 is a helical coil of electrically-conductive material, such as copper. In some embodiments, the magnetic field generator 112 may comprise a magnetically permeable core around which the coil 114 is wound. Such a magnetically permeable core concentrates the magnetic flux produced by the coil 114 in use and makes a more powerful magnetic field. The magnetically permeable core may be made of iron, for example. In some embodiments, the magnetically permeable core may extend only partially along the length of the coil 114, so as to concentrate the magnetic flux only in certain regions. In some embodiments, the coil may be a flat coil. That is, the coil may be a two-dimensional spiral.

In this embodiment, the coil 114 is in a fixed position relative to the heater 115 and the heating zone 111. In this embodiment, the coil 114 encircles the heater 115 and the heating zone 111. In this embodiment, the coil 114 extends along a longitudinal axis that is substantially aligned with a longitudinal axis A-A of the heating zone 111. In this embodiment, the aligned axes are coincident. In a variation to this embodiment, the aligned axes may be parallel to each other. However, in other embodiments, the axes may be oblique to each other. Moreover, in this embodiment, the coil 114 extends along a longitudinal axis that is substantially coincident with a longitudinal axis of the heater 115. This can help to provide more uniform heating of the heater 115 in use, and can also aid manufacturability of the apparatus 100. In other embodiments, the longitudinal axes of the coil 114 and the heater 115 may be aligned with each other by being parallel to each other, or may be oblique to each other.

In this embodiment, the device 116 for passing a varying current through the coil 114 is electrically connected between the electrical power source 113 and the coil 114. In this embodiment, the controller 117 also is electrically connected to the electrical power source 113, and is communicatively connected to the device 116 to control the device 116. More specifically, in this embodiment, the controller 117 is for controlling the device 116, so as to control the supply of electrical power from the electrical power source 113 to the coil 114. In this embodiment, the controller 117 comprises an integrated circuit (IC), such as an IC on a printed circuit board (PCB). In other embodiments, the controller 117 may take a different form. In some embodiments, the apparatus may have a single electrical or electronic component comprising the device 116 and the controller 117. The controller 117 is operated in this embodiment by user-operation of the user interface 118. In this embodiment, the user interface 118 is located at the exterior of the body 110. The user interface 118 may comprise a push-button, a toggle switch, a dial, a touchscreen, or the like. In other embodiments, the user interface 118 may be remote and connected to the rest of the apparatus wirelessly, such as via Bluetooth.

In this embodiment, operation of the user interface 118 by a user causes the controller 117 to cause the device 116 to cause an alternating electrical current to pass through the coil 114, so as to cause the coil 114 to generate an alternating magnetic field. The coil 114 and the heater 115 of the apparatus 100 are suitably relatively positioned so that the alternating magnetic field produced by the coil 114 penetrates the heating material of the heater 115. When the heating material of the heater 115 is an electrically-conductive material, this may cause the generation of one or more eddy currents in the heating material. The flow of eddy currents in the heating material against the electrical resistance of the heating material causes the heating material to be heated by Joule heating. In this embodiment, the heating material is made of a magnetic material, and so the orientation of magnetic dipoles in the heating material changes with the changing applied magnetic field, which causes heat to be generated in the heating material.

The heater 115 outputs substantially the same amount of heat at each position along its length. Therefore, the foam 20 of the article 4 is substantially uniformly heated along its length. As the densities of the first and second portions 20*a* of the foam 20 differ from each other, one of the first and second portions 20*a*, 20*b* of the foam 20 may be heated before the other in use. For example, the denser portion of the foam 20 may heat quicker than the less dense portion of the foam.

In this embodiment, an impedance of the coil 114 of the magnetic field generator 112 is equal, or substantially equal, to an impedance of the heater 115. If the impedance of the heater 115 were instead lower than the impedance of the coil 114, then the voltage generated across the heater 115 in use may be lower than the voltage that may be generated across the heater 115 when the impedances are matched. Alternatively, if the impedance of the heater 115 were instead higher than the impedance of the coil 114, then the electrical current generated in the heater 115 in use may be lower than the current that may be generated in the heater 115 when the impedances are matched. In embodiments of the system 1000 comprising one of the articles 2, 3, of FIGS. 2 and 3, similarly the impedance of the coil 114 may be equal, or substantially equal, to an impedance of the part of the article 2, 3, 5, 6 comprising heating material. Matching the impedances may help to balance the voltage and current to maximize the heating power generated at the heater 115 or heating material of the article 2, 3, 5, 6 when heated in use. In some embodiments, the impedance of the device 116 may be equal, or substantially equal, to a combined impedance of the coil 114 and the heater 115.

The apparatus 100 of this embodiment comprises a temperature sensor 119 for sensing a temperature of the heating zone 111. The temperature sensor 119 is communicatively connected to the controller 117, so that the controller 117 is able to monitor the temperature of the heating zone 111. On the basis of one or more signals received from the temperature sensor 119, the controller 117 may cause the device 116 to adjust a characteristic of the varying or alternating electrical current passed through the coil 114 as necessary, in order to ensure that the temperature of the heating zone 111 remains within a predetermined temperature range. The characteristic may be, for example, amplitude or frequency or duty cycle. Within the predetermined temperature range, in use the smokable material within an article 1, 2, 3, 4, 5, 6 located in the heating zone 111 is heated sufficiently to volatilize at least one component of the smokable material without combusting the smokable material. Accordingly, the controller 117, and the apparatus 100 as a whole, is arranged to heat the smokable material to volatilize the at least one component of the smokable material without combusting the smokable material. In some embodiments, the temperature range is about 50° C. to about 300° C., such as between about 50° C. and about 250° C., between about 50° C. and about 150° C., between about 50° C. and about 120° C., between about 50° C. and about 100° C., between about 50° C. and about 80° C., or between about 60° C. and about 70° C. In some embodiments, the temperature range is between about 170° C. and about 220° C. In other embodiments, the temperature range may be other than this range. In some embodiments, the upper limit of the temperature range could be greater than 300° C. In some embodiments, the temperature sensor 119 may be omitted. In some embodiments, the heating material may have a Curie point temperature selected on the basis of the maximum temperature to which it is desired to heat the heating material, so that further heating above that temperature by induction heating the heating material is hindered or prevented.

In an embodiment that is a variation to the system 1000 shown in FIG. 9, the coil 114 may be arranged to generate an alternating or otherwise varying magnetic field that penetrates heating material of the article 2, 3, 5, 6 when the apparatus 100 and the article 2, 3, 5, 6 are suitably relatively positioned with the article 2, 3, 5, 6 in the heating zone 111. When the heating material of the article 2, 3, 5, 6 is an electrically-conductive material, this may cause the generation of one or more eddy currents in the heating material. The flow of eddy currents in the heating material against the electrical resistance of the heating material causes the heating material to be heated by Joule heating. As mentioned above, when the heating material is made of a magnetic material, the orientation of magnetic dipoles in the heating material changes with the changing applied magnetic field, which causes heat to be generated in the heating material. In some embodiments, heat generated in the heating material of the heater 115 of the apparatus 100 could be transferred to the article 2, 3, 5, 6 to heat, or further heat, the smokable material therein when the portion of the article is in the heating zone 111. In other embodiments, the heater 115 may be omitted from the apparatus 100.

In each of the above described embodiments, the apparatus 100 is configured to cause heating of heating material, and thus the smokable material, using induction heating. However, in other embodiments, the apparatus may be configured to use a different form of heating, such as resistive heating. In some such embodiments, the magnetic field generator 112 may be omitted from the apparatus 100.

In each of the above described embodiments, the smokable material comprises tobacco. However, in respective variations to each of these embodiments, the smokable material may consist of tobacco, may consist substantially entirely of tobacco, may comprise tobacco and smokable material other than tobacco, may comprise smokable material other than tobacco, or may be free from tobacco. In some embodiments, the smokable material may comprise a vapor or aerosol forming agent or a humectant, such as glycerol, propylene glycol, triacetin, or diethylene glycol.

An article embodying the present disclosure may be a cartridge, for example.

In each of the above described embodiments, the article 1, 2, 3, 4, 5, 6 is a consumable article. Once all, or substantially all, of the volatilizable component(s) of the smokable material in the article 1, 2, 3, 4, 5, 6 has/have been spent, the user may remove the article 1, 2, 3, 4, 5, 6 from the apparatus and dispose of the article 1, 2, 3, 4, 5, 6. The user may subsequently re-use the apparatus with another of the articles 1, 2, 3, 4, 5, 6. However, in other respective embodiments, the article 1, 2, 3, 4, 5, 6 may be non-consumable, and the apparatus and the article 1, 2, 3, 4, 5, 6 may be disposed of together once the volatilizable component(s) of the smokable material has/have been spent.

In some embodiments, the apparatus discussed above is sold, supplied or otherwise provided separately from the articles 1, 2, 3, 4, 5, 6 with which the apparatus is usable. However, in some embodiments, the apparatus and one or more of the articles 1, 2, 3, 4, 5, 6 may be provided together as a system, such as a kit or an assembly, possibly with additional components, such as cleaning utensils.

In order to address various issues and advance the art, the entirety of this disclosure shows by way of illustration and example various embodiments in which the claimed invention may be practiced and which provide for superior articles for use with apparatus for heating smokable material to volatilize at least one component of the smokable material, and superior systems comprising such apparatus and such articles. The advantages and features of the disclosure are of a representative sample of embodiments only, and are not exhaustive and/or exclusive. They are presented only to assist in understanding and teach the claimed and otherwise disclosed features. It is to be understood that advantages, embodiments, examples, functions, features, structures and/or other aspects of the disclosure are not to be considered limitations on the disclosure as defined by the claims or limitations on equivalents to the claims, and that other embodiments may be utilized and modifications may be made without departing from the scope and/or spirit of the disclosure. Various embodiments may suitably comprise, consist of, or consist in essence of, various combinations of the disclosed elements, components, features, parts, steps, means, etc. The disclosure may include other inventions not presently claimed, but which may be claimed in future.

The invention claimed is:

1. An article for use with an apparatus for heating smokable material to volatilize at least one component of the smokable material, the article comprising:
   a foam comprising smokable material and comprising gas dispersed in a solid medium, wherein the foam is in the form of a rod configured to allow air to be drawn in through one end, to pass through the foam, and to be drawn out of the opposite end; and
   heating material that is heatable by penetration with a varying magnetic field, wherein the heating material is in thermal contact with the smokable material.

2. The article of claim 1, wherein the solid medium comprises the smokable material.

3. The article of claim 1, wherein the foam is an open-cell foam.

4. The article of claim 1, wherein the foam extends from one end of the article to an opposite end of the article.

5. The article of claim 1, wherein a first portion of the foam has a first density, wherein a second portion of the foam has a second density, and wherein the second density is greater than the first density.

6. The article of claim 5, wherein the article is elongate, and wherein the first portion and the second portion of the foam are located at different positions along a length of the article.

7. The article of claim 1, wherein the foam is fixed or adhered to the heating material.

8. The article of claim 1, wherein the heating material is in the form of a body that extends from one end of the article to an opposite end of the article.

9. The article of claim 1, wherein the heating material comprises one or more materials selected from the group consisting of: an electrically-conductive material, a magnetic material, and a magnetic electrically-conductive material.

10. The article of claim 1, wherein the heating material comprises a metal or a metal alloy.

11. The article of claim 1, wherein the heating material comprises one or more materials selected from the group consisting of: aluminum, gold, iron, nickel, cobalt, conductive carbon, graphite, plain-carbon steel, stainless steel, ferritic stainless steel, copper, and bronze.

12. The article of claim 1, comprising elements dispersed through the foam, wherein each of the elements comprises heating material that is heatable by penetration with a varying magnetic field, and wherein the heating material is in thermal contact with the smokable material.

13. The article of claim 12, wherein the elements are dispersed evenly, or substantially evenly, through the foam.

14. The article of claim 12, wherein each of the elements comprises a closed circuit of the heating material.

15. The article of claim 1, wherein the smokable material comprises at least one of tobacco or one or more humectants.

16. A system, comprising:
   an article including a foam comprising smokable material and heating material that is heatable by penetration with a varying magnetic field, wherein the heating material is in thermal contact with the smokable material, and wherein the foam comprises gas dispersed in a solid medium and is in the form of a rod configured to allow air to be drawn in through one end, to pass through the foam, and to be drawn out of the opposite end; and an apparatus for heating the smokable material to volatilize at least one component of the smokable material, wherein the apparatus comprises a heating zone for receiving at least a portion of the article.

17. The system of claim 16, wherein the apparatus is for heating the smokable material to volatilize at least one component of the smokable material without combusting the smokable material.

\* \* \* \* \*